(12) United States Patent
Mylari

(10) Patent No.: US 8,440,723 B2
(45) Date of Patent: May 14, 2013

(54) METFORMIN SALTS OF SALICYLIC ACID AND ITS CONGENERS

(76) Inventor: Banavara L. Mylari, Lutz, FL (US)

( * ) Notice: Subject to any disclaimer, the term of this patent is extended or adjusted under 35 U.S.C. 154(b) by 0 days.

(21) Appl. No.: 13/450,094

(22) Filed: Apr. 18, 2012

(65) Prior Publication Data

US 2012/0289485 A1 Nov. 15, 2012

Related U.S. Application Data

(60) Provisional application No. 61/485,091, filed on May 11, 2011.

(51) Int. Cl.
*A01N 37/52* (2006.01)
(52) U.S. Cl.
USPC ............ 514/635; 514/159; 514/634; 564/233
(58) Field of Classification Search ........................ None
See application file for complete search history.

(56) References Cited

U.S. PATENT DOCUMENTS 3,174,901 A * 3/1965 Sterne ........................... 514/635
2009/0298796 A1 * 12/2009 Shoelson et al. .............. 514/159

* cited by examiner

*Primary Examiner* — Sudhakar Katakam
(74) *Attorney, Agent, or Firm* — Robert D. Katz; Eaton & Van Winkle LLP.

(57) ABSTRACT

The present invention relates to compounds,

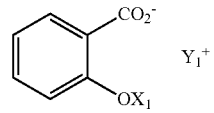

Formula VI

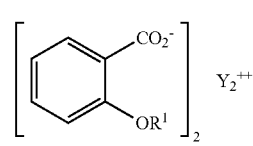

Formula VII intermediates used in the preparation of such compounds, processes for the preparation of such compounds of the formula VI and formula VII and such intermediates, pharmaceutical compositions comprising such compounds of the formula VI and such compounds of the formula VII, and the uses of such compounds of the formula VI and such compounds of the formula VII as antidiabetic, pre-antidiabetic, antiobesity and cardioprotective agents.

26 Claims, No Drawings

METFORMIN SALTS OF SALICYLIC ACID AND ITS CONGENERS

CROSS REFERENCE TO RELATED APPLICATION

The present application claims priority from the U.S. Provisional Patent Application No. 61/485,091 filed on May 11, 2011, the contents of which are herein incorporated by reference.

BACKGROUND OF THE INVENTION

The present invention relates to metformin salts, processes for preparing such salts, intermediates used in the preparation of such salts, processes for preparing such intermediates, pharmaceutical compositions comprising such salts and methods of treating diabetes in mammals comprising administering to said mammals said salts or said compositions.

Metformin, also known by other names including N,N-dimethylimidodicarbonimidic diamide and 1,1-dimethyl-biguanide, is a known compound and it is disclosed in J. Chem. Soc., 1922, 121, 1790. The compound and its preparation and use are also disclosed, for example, in U.S. Pat. No. 3,174,901. Metformin is orally effective in the treatment of type 2 diabetes. Metformin is currently marketed in the United States in the form of its hydrochloride salt as an anti-hyperglycemic agent (formula I). Metformin hydrochloride can be purchased commercially and can also be prepared, for example, as disclosed in J. Chem. Soc., 1922, 121, 1790. It is postulated that metformin decreases hepatic glucose production and improves insulin sensitivity by increasing peripheral glucose uptake and utilization. Metformin hydrochloride is approved by the United States Food & Drug Administration for the therapeutic treatment of diabetes and it is widely regarded as the drug of choice for most patients with type 2 diabetes.

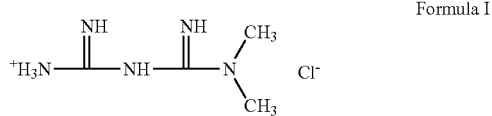

Formula I

U.S. Pat. No. 7,973,073 B2 (Mylari et al) describes use of metformin R-(+) lipoate as being useful for treating diabetes or diabetic complications.

According to United Kingdom Perspective Diabetes Study (UKPDS) (Clarke et al. Diabetologia, 2005, 48, 868-877), metformin therapy was cost-saving and increased quality-adjusted life expectancy. In the UKPDS, overweight and obese patients randomized to initial therapy with metformin experienced significant reductions in myocardial infarction and diabetes-related deaths. Metformin does not promote weight gain and has beneficial effects on several cardiovascular risk factors. Accordingly, metformin is widely regarded as the drug of choice for most patients with Type 2 diabetes.

Prediabetes is a syndrome. Many patients with type 2 diabetes and with a prediabetic condition known as metabolic syndrome suffer from a variety of lipid disorders including elevated triglycerides. The body uses triglycerides to store fat but high (>200 mg/dl) and very high (>500 mg/dl) triglycerides are associated with atherosclerosis which increases the patients risk of heart attack and stroke.

Incipient diabetes with impaired glucose tolerance is another prediabetic condition. Overall, type 2 diabetes and incipient diabetes with impaired glucose tolerance, are intimately intertwined with obesity, hyperlipidemia, including hypertriglyceridemia, and cardiovascular complications including arrhythmia, cardiomyopathy, myocardial infarction, stroke and heart failure. Clinically, pre-diabetes means that blood sugar level is higher than normal, but it's not yet increased enough to be classified as type 2 diabetes. Still, without intervention, prediabetes is likely to become type 2 diabetes over time It is a matter of great concern that many patients are known to develop resistance to metformin over time. According to Shoelson et al, in The Journal of Clinical Investigation, 2006, 116, 1793-1801 increased levels of markers and mediators of inflammation correlate with incident type 2 diabetes. Subsequently, A. B. Goldfine et al, in Annals of Internal Medicine, 2010, 152, 346-357 and references cited therein, have shown that the compound of formula III, also known as salsalate, lowers blood glucose, $HbA_{1c}$ levels, triglycerides, free fatty acid and C-reactive protein in patients with type 2 diabetes. Also, salsalate was said to improve glucose utilization and was said to increase circulating insulin. Furthermore it was said to increase adiponectin concentrations. Unlike any other known antidiabetic, salsalate is thought to target the inflammation component of diabetes. Thus salsalate may provide a new avenue for treatment. Very recently, a new aspect of salsalate has come to light. According to Nixon et al, Diabetes Publish Ahead of Print, published online Feb. 22, 2012, the anti-inflammatory agent salsalate alters glucocorticoid metabolism in mice and humans in a pattern that differs between liver and subcutaneous adipose tissue. Down regulation of intra-adipose 11β-hydroxysteroid dehydrogenase-1 may contribute to the insulin sensitizing effect of salicylates. Also, Shoelson et al (US 2011/0021468 A1, Jan. 27, 2011) have described the use of salsalate in atherosclerotic cardiovascular disease. Salsalate is thought to be a prodrug of salicylic acid (formula II). Similarly the compound of the formula IV and the compound of the formula V can also be regarded as prodrugs of salsalate and salicylic acid. It is well known in the art that highly water soluble medicinal preparations, when administered orally, result in efficient absorption of such preparations from the gastrointestinal tract into systemic circulation. Another hallmark of such preparations is the rate at which they are absorbed into systemic circulation resulting in high concentration of the active agent or agents in the blood. According to The Merck Index, Eleventh Edition, 1 g. of salicylic acid is soluble in 460 mL of water (i.e. water solubility is 2.17 mg/mL) and salsalate is practically insoluble in water. The salts of the present invention are markedly more water soluble to provide concomitant delivery of both metformin and salicylic acid and its congeners, thus providing a dual action in targeting both hepatic glucose production and inflammation aspects of type 2 diabetes in patients with type 2 diabetes. Furthermore, the new salts would offer a patient friendly dosage form of two active therapies in a fixed dosage combination with increased reliability for daily patient compliance. Juvisync, recently approved by the United States Food and Drug Administration, is a contemporary example of a fixed combination of two widely used drugs for reliability of usage and patient convenience (FDA News Release. Oct. 7, 2011).

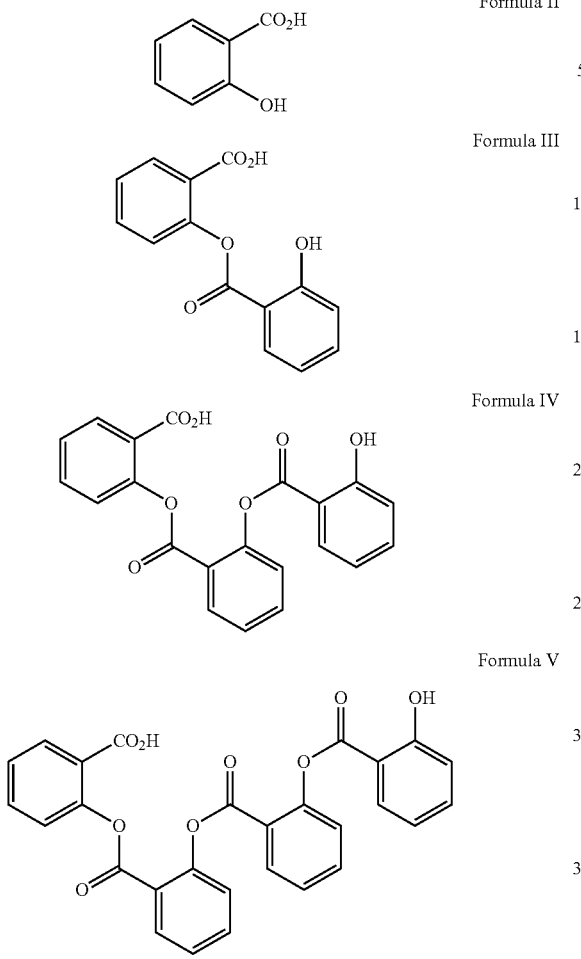

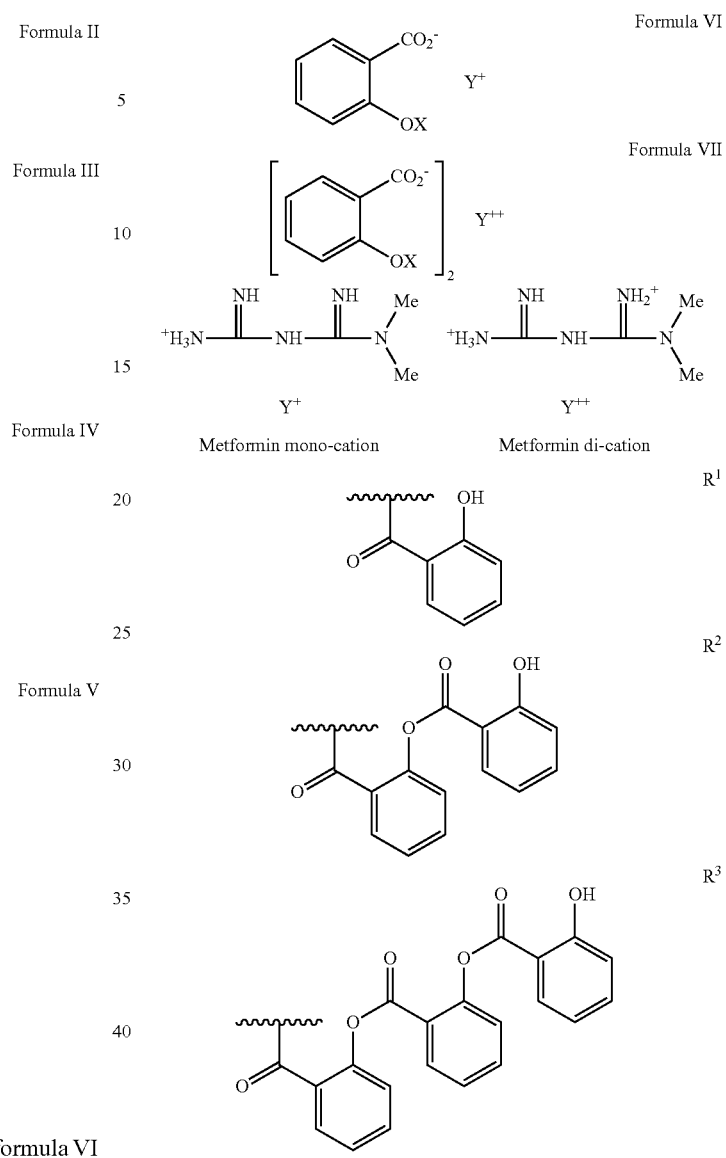

SUMMARY OF THE INVENTION

The present invention relates to compounds of formula VI and formula VII wherein X is selected from H, $R^1$, $R^2$, and $R^3$, $Y^+$ is metformin mono-cation and $Y^{++}$ is metformin di-cation, wherein $R^1$, $R^2$, $R^3$, $Y^+$ and $Y^{++}$ are as depicted below These compounds are also referred to herein as the metformin salts of the present invention. The compounds wherein X is H and $Y^+$ is metformin mono-cation may commonly be referred to as metformin mono-salts of salicylic acid. The compounds wherein X is H and $Y^{++}$ is metformin di-cation may commonly referred to as metformin bis-salt of salicylic acid. The compounds wherein X is $R^1$ and $Y^+$ is metformin mono-cation may commonly be referred to as metformin mono-salts of salsalate (salsalate is also known as (2-(2-hydroxybenzoyl) oxybenzoic acid). The compounds wherein X is $R^1$ and $Y^{++}$ is metformin di-cation may commonly be referred to as metformin bis-salts of salsalate.

The present invention also relates to the compounds of formula IV and formula V depicted below which may commonly be referred to respectively, as tri-salicylic acid and tetra-salicylic acids. These compounds are useful as intermediates in preparing the metformin salts of the present invention.

It should be understood that the location of the positive charge(s) in metformin mono-cation and metformin di-cation (which may also be referred to as metformin bis-cation) is illustrative only and it (they) could be located on other nitrogen atoms in metformin.

Metformin mono salt of salicylic acid has a water solubility of 900 mg/mL and metformin mono salt of salicylsalicylic acid has a water solubility of 36 mg/mL. So, compared to solubility values documented for salicylic acid and salicylsalicylic acid, metformin mono salt of salicylic acid is 415 times more soluble than salicylic acid and metformin mono salt of salicylsalicylic acid is practically infinitely more soluble than salicylsalicylic acid.

The compounds of the present invention include any polymorphs, solvates, and hydrates of the metformin salts described herein In one embodiment of the present invention, the metformin salts of the present invention are the mono-salt of salicylic acid, the bis-salt of salicylic acid, the mono-salt of salsalate, and the bis-salt of salsalate. In another embodiment, they may be the mono-salt of tri-salicylic acid, the bis-salt of tri-salicylic acid, the mono-salt of tetra-salicylic acid and the bis-salt of tetra-salicylic acid. In another embodiment, the metformin salts of the present invention are the bis-salt of salicylic acid, the mono-salt of salsalate and the bis-salt of salsalate.

The present invention also relates to a pharmaceutical composition comprising a salt of the present invention and a pharmaceutically acceptable carrier.

In one embodiment, the present invention relates to a pharmaceutical composition for the treatment of diabetes in mammals comprising an anti-diabetes effective amount of a metformin salt of the present invention and a pharmaceutically acceptable carrier. In one embodiment said mammals are humans.

The present invention also relates to a method of treating diabetes in a mammal comprising administering to said mammal a metformin salt of the present invention. In one embodiment of the invention the mammal is a human The present invention also relates to a method of treating diabetes in a mammal comprising administering to a mammal in need of said treatment an anti-diabetic effective amount of a metformin salt of the present invention. In one embodiment of the invention the mammal is a human.

The present invention also relates to a method of treating prediabetes in a mammal comprising administering to a mammal in need of said treatment an anti-prediabetic effective amount of a metformin salt of the present invention. In one embodiment of the invention the mammal is a human.

The present invention also relates to a method of treating obesity in a mammal comprising administering to a mammal in need of said treatment an antiobesity effective amount of a metformin salt of the present invention. In one embodiment of the invention the mammal is a human.

The present invention also relates to a method of treating atherosclerotic cardiovascular disease in a mammal comprising administering to a mammal in need of said treatment an anti-atherosclerotic cardiovascular disease effective amount of a metformin salt of the present invention. In one embodiment of the invention the mammal is a human.

One embodiment of the present invention relates to a unit dosage form comprising a metformin salt of this invention.

One embodiment of the present invention relates to a kit comprising a unit dosage comprising a metformin salt of this invention with instructions on how to use the kit and with provision for at least one container for holding the unit dosage form.

The terms "treating", "treat", or "treatment" as used herein include curative, preventive (e.g., prophylactic) and palliative treatment.

The present invention also relates to a process for preparing a compound of the formula XI by reacting a compound of formula VIII with salicylic acid (formula IX). This reaction herein is referred to as a coupling reaction and is carried out in the presence of coupling reagents such as dicyclohexylcarbodiimide in alchohol (e.g., ethanol), hydrocarbon (e.g., toluene) and ether (e.g., tetrahydrofuran) solvents. The reaction is conducted at room temperature to reflux temperature of the solvent used. The reaction is conducted from between 1 hour to overnight. Other coupling reagents that can be employed include diisopropylcarbodiimide, ethyl-($N^1,N^1$-dimethylamino)propylcarbodiimide hydrochloride and 3-(diethylphosphoryloxy)-1,2,3-benzotriazin-4(3H)-one.

The present invention also relates to a process for preparing a compound of the formula XII. A compound of formula XI is subjected to a coupling reaction with a compound of formula IX, as described above, to prepare a compound of the formula XII.

The present invention also relates to a process for preparing a compound of the formula XIII. A compound of the formula XII is subjected to a coupling reaction with the compound of the formula IX, as described above, to prepare compound of the formula XIII.

The present invention also relates to a process for preparing a compound of the formula IV. Compound of the formula XII is reacted with a heterogeneous palladium on carbon (Pd/C) catalyst in the presence of hydrogen gas or a hydrogen transfer agent, e.g. ammonium formate or isopropanol, to obtain a compound of the formula IV.

The present invention also relates to a process for preparing a compound of the formula V. A compound of the formula XIII is reacted with a heterogeneous palladium on carbon (Pd/C) catalyst in the presence of hydrogen gas or a hydrogen transfer agent, e.g. ammonium formate or isopropanol, to obtain a compound of the formula V.

DETAILED DESCRIPTION OF THE INVENTION

The metformin salts of the present invention, i.e., metformin mono-salt of salicylic acid, metformin bis-salt of salicylic acid, metformin mono-salt of salsalate, metformin bis-salt of salsalate, metformin mono-salt of tri-salicylic acid, metformin bis-salt of tri-salicylic acid, metformin mono-salt of tetra-salicylic acid and metformin bis-salt of tetra-salicylic acid, can be prepared as set forth below.

One equivalent of metformin free base, prepared according the method of U.S. Pat. No. 3,957,853 (hereby incorporated herein by reference) may be dissolved in an appropriate reaction inert solvent. The solvent may be a polar solvent such as water. As used herein, the expression "reaction inert solvent" refers to a solvent or a mixture of solvents which doesn't interact with starting materials, reagents, intermediates or products in a manner which adversely affects the yield of the desired product. Preferred solvents include methanol, ethanol, n-propanol, isopropanol, acetonitrile, acetone, ethyl methyl ketone, diethyl ketone and methyl isobutyl ketone. Particularly preferred solvents for this reaction are acetonitrile, acetone and methyl isobutyl ketone. To this solution may be added a solution of one equivalent of salicylic acid, salsalate (Both salicylic acid and salsalate are commercially available), also known as (2-(2-hydroxybenzoyl)oxybenzoic acid), trisalicylic acid or tetrasalicylic acid in a reaction inert solvent. The reaction mixture can be stirred at about ambient temperature to about the reflux temperature of the solvent being used for about two hours to about six hours, preferably at ambient temperature for about two hours. The metformin mono salts of this invention can be isolated from the reaction mixture by methods well known to those skilled in the art, including according to the method of U.S. Pat. No. 3,957,853.

The metformin bis-salts of the present invention can be prepared according to the above procedure, but by using two equivalents, instead of one equivalent, of salicylic acid, salsalate, trisalicylic acid or tetrasalicylic acid.

One equivalent of metformin freebase may be fused with one equivalent of salicylic acid, salicylsalicylic acid, trisalicylic acid, or tetrasalicylic acid, referred to as reactants, at a temperature from about 100 degree C. to 200 degree C. The metformin mono salts of this invention can be isolated from the reaction mixture by methods well known to those skilled in the art.

One equivalent of metformin freebase may be fused with two equivalents of salicylic acid, salicylsalicylic acid, trisalicylic acid, or tetrasalicylic acid, referred to as reactants, at a temperature from about 100 degree C. to 200 degree C. The metformin bis-salts of this invention can be isolated from the reaction mixture by methods well known to those skilled in the art.

Trisalicylic acid is described by Don Carlos Monserrat Vidal et al (ES 8308897 A1, "Procedimiento Para Obtencion De Polimeros Del Acido 2-Hydroxibenzoico") and tetrasalicylic acid is described by O. Shulga and J. Dunn (Thermochimica Acta. 2004, 410, 15-21). Furthermore, trisalicylic acid and tetrasalicylic acid can be prepared by adapting procedures described by Galzigna, L. et al. in Farmaco, 1993, 48(1), 95-103 with the title "Synthesis and some properties of two salsalate derivatives."

The starting materials for the preparation of metformin mono-salt and bis-salt of trisalicylic acid and tetrasalicylic acid can also be prepared according to Scheme I. In this scheme, coupling and reductive debenzylation reactions are performed under conditions well known to those skilled in the art. For example, the coupling reaction can be carried out according to the method of Castro et al. in Tetrahedron Lett. 1975, 1219-1222 and Sliedregt et al. in Tetrahedron Lett. 1996, 37, 4237, 4237-4240, using reagents such as dicyclohexylcarodiimide, diisopropylcarbodiimide, and ethyl-($N^1$, $N^1$-dimethylamino)propylcarbodiimide hydrochloride. The coupling reaction can also be carried out according to the method of Li et al. in Org. Lett. 1999, 1, 91-93, using 3-(diethylphosphoryloxy)-1,2,3-benzotriazin-4(3H)-one. Debenzylation can be carried out according to procedures described in J. P. Chen, et al., Catalysis of Organic Reactions, Ed. By D. Morrell, Marcel Dekker, New York, pp. 313-328, (2002). Typically, debenzylation can be performed using a heterogeneous palladium on carbon (Pd/C) catalyst in the presence of hydrogen gas or a hydrogen transfer agent, e.g. ammonium formate or isopropanol.

Scheme 1

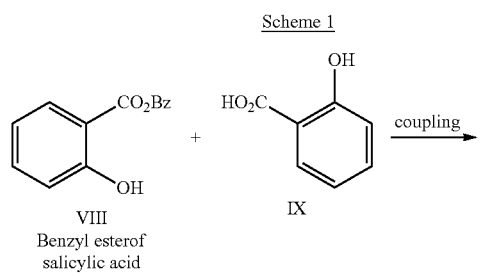

VIII
Benzyl ester of
salicylic acid

IX coupling

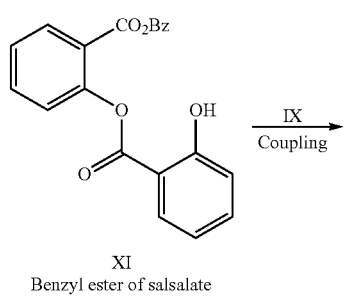

XI
Benzyl ester of salsalate

IX
Coupling

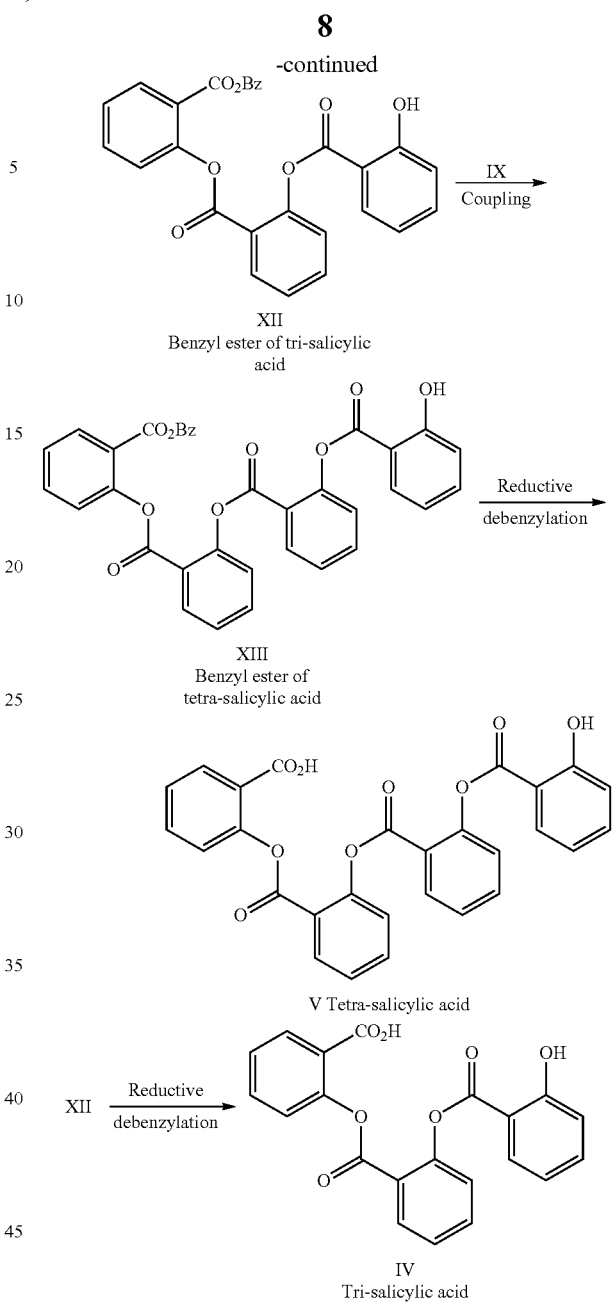

XII
Benzyl ester of tri-salicylic
acid

XIII
Benzyl ester of
tetra-salicylic acid

Reductive
debenzylation

V Tetra-salicylic acid

XII
Reductive
debenzylation

IV
Tri-salicylic acid

The compounds of the present invention intended for pharmaceutical use may be administered alone or in combination with one or more other compounds of the invention or in combination with one or more other drugs (or as any combination thereof). Examples of such other drugs are antidiabetics (e.g., sulfonylureas, DPPIV inhibitors, SGLT-2 inhibitors) antihypertensives (e.g., ACE inhibitors, AR blockers, diuretics such as hydrochlorothiazide) and antihyperlipidemics (e.g., statins, fibrates, polyunsaturated acids such as eicosapentaenoic acid). Generally, the compounds of the present invention will be administered as a formulation in association with a pharmaceutically acceptable carrier comprising one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Formulations suitable for oral administration include solid formulations, such as tablets, capsules containing particulates, liquids, or powders; lozenges (including liquid-filled), chews; multi- and nano-particulates; gels, solid solution, liposome, films (including muco-adhesive), ovules, sprays and liquid formulations.

Dosage

For administration to human patients, the total daily dose of the compounds of the invention is typically in the range 1 g to 12 g depending, of course, on the mode of administration. In one embodiment the total daily dose is in the range 1 g to 10 g and in another embodiment the total daily dose is in the range 4 g to 8 g. The total daily dose may be administered in single or divided doses.

These dosages are based on an average human subject having a weight of about 65 kg to 70 kg. The physician will readily be able to determine doses for subjects whose weight falls outside this range, such as infants and the elderly.

The pharmaceutical composition may, for example, be in a form suitable for oral administration as a tablet, capsule, pill, powder, sustained release formulations, solution, or suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier and a compound according to the invention as an active ingredient. In addition, it may include other medicinal or pharmaceutical agents, carriers, adjuvants, etc.

Suitable pharmaceutical carriers include inert diluents or fillers, water and various organic solvents. The pharmaceutical compositions may, if desired, contain additional ingredients such as flavorings and binders.

[Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).]

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Compounds of the formula VI and the formula VII can be tested for anti-diabetes activity as follows. Male Wistar rats 8-10 weeks of age 210-230 g. of body weight (bw) are used. The rats are housed at temperature of 18-21° C. on a 12 hour light-dark cycle. Rats are fed on a stock laboratory diet (59% carbohydrates, 17% protein, 3% fat, 21% minerals, water, and cellulose) and are allowed water ad libitum. Diabetes mellitus is induced in Wistar male rats by two intravenous injections of alloxan (40 mg/kg bw) in the tail vein. The rats are used in experiments 6 days after the first alloxan injection. Fasting glucose, insulin, total cholesterol, and triglycerides levels of these animals are recorded. Then rats are treated with metformin hydrochloride (100-300 mg/kg bw) for the next 5 days. On the sixth day. Fasting glucose, insulin, total cholesterol, and triglycerides levels of these animals are recorded.

Compounds of the formula VI and the formula VII can also be tested for anti-diabetes activity as follows. Spontaneously diabetic Bio-Bred (BB/W) rats from the colony maintained at the University of Massachusetts Medical Center, Worcester, were used in this study. BB/W rats were chosen for the current study because the BB/W rats have been considered a useful model of autoimmune human insulin-dependent diabetes DM). Like human IDDM, spontaneous diabetes appears during adolescence, with an abrupt clinical onset characterized by weight loss, hyperglycemia, hypoinsulinemia, and ketonuria. As in the case of human diabetics, pathological changes in retina, myocardium, liver, kidney, bone metabolism and peripheral nerves have all been well documented in BB rats, as described in *Diab. Metab. Rev.*, 8:9 (1992). The BB/W rats were 3 to 4 months old and weighed about 300 to 350 g. The BB/W rats received daily insulin, which was discontinued 24 h prior to performing the isolated heart perfusion studies, leading to a hyperglycemic state. The rats were acutely diabetic, receiving 2.02±0.04 units of insulin daily, and had been diabetic for at least 12±3 days. The mean blood glucose levels in these diabetic rats were 386±24 mg/dL. The age-matched non-diabetic controls had mean blood glucose levels of 92±12 mg/dL.

Animal models to determine the effects of compounds of the invention on diabetes and complications of diabetes have been reviewed by Tirabassi et al., ILAR Journal, 2004, 45, 292-302. Antidiabetic activity may also be tested according to protocols described in the following patents: U.S. Pat. Nos. 4,340,605; 4,342,771; 4,367,234; 4,617,312; 4,687,777 and 4,703,052. Additional references relevant to this application include the following: French Patent 2796551 and United States Published Patent Application No. 20030220301.

Efficacy in treating prediabetes can be determined according to protocols described by Armato et al in Endocrinology Practice, 2011, Nov. 8: 1-21 (Epub ahead of print).

Efficacy in ameliorating atherosclerotic cardiovascular disease can be determined according to Shoelson et al (US 2011/0021468 A1, Jan. 27, 2011).

EXAMPLE 1

Metformin mono-salt of salicylic acid

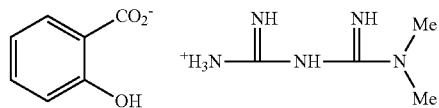

N,N-dimethylimidodicarbonimidic diamide
(Metformin free base)

N,N-dimethylimidodicarbonimidic diamide hydrochloride (Formula I) (4.06 g, 24.5 mmol) was dissolved in 1N sodium hydroxide (24.5 mL, 24.5 mmol) and stirred at room temperature for 30 minutes. The solution was concentrated in vacuo and to the residue was added EtOH (80 mL). The mixture was carefully concentrated to azeotropically remove water. To the resulting solid was added EtOH (40 mL) and the suspension was filtered to remove precipitated sodium chloride. The filtrate was concentrated and the resulting solid was placed on high vacuum overnight to yield 3.02 g (95%) of metformin free base as a white solid.

{[Amino(imino)methyl]amino}(dimethylamino) methaniminium salicylate (Metformin salt of salicylic acid)

N,N-Dimethylimidodicarbonimidic diamide (metformin free base) (1.66 g, 12.8 mmol) was dissolved in acetonitrile (45 mL) and the resulting solution was filtered through a medium frit to remove a small amount of sodium chloride that precipitated. To the filtrate was added dropwise at room temperature (over a 2 minute period) a solution of salicylic acid (1.42 g, 10.3 mmol) in acetonitrile (20 mL). The reaction solution became warm and a white solid precipitated about 1 minute after the addition was complete. After stirring for 1 h at room temperature, the mixture was chilled to 0° C. for 1 h. The white solid was filtered and the solid was washed with 20 mL ice-cold acetonitrile. The material was dried for 5 minutes on the frit followed by transfer of the solid to a round-bottom flask and the material was left under high vacuum overnight to yield 2.27 g (82%) of the title compound as a crystalline white solid. MP 152-154° C.; $^1$H NMR (400 MHz, MeOD) 7.82 (dd, J=7.67, 1.66 Hz, 1 H), 7.26 (m, 1 H), 6.76 (m, 2 H), 3.03 (s, 6 H); $^{13}$C NMR (101 MHz, MeOD) 176.31, 162.72, 161.33, 160.57, 133.87, 131.77, 120.38, 119.10, 117.25, 38.09; MS (ESI−) for $C_7H_6O_3$ m/z 137.1 (M-H)$^-$.

EXAMPLE 2

Metformin mono-salt of salicylsalicylic acid

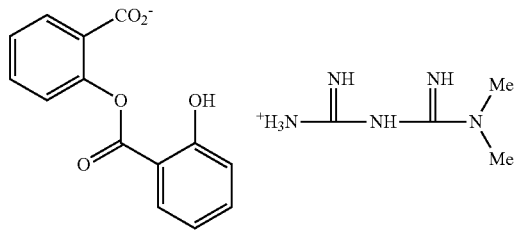

{[Amino(imino)methyl]amino}(dimethylamino) methaniminium 2-[(2-hydroxybenzoyl)oxy]benzoate Metformin salt of salicylsalicylic acid N,N-Dimethylimidodicarbonimidic diamide (metformin free base) (1.21 g, 9.37 mmol) was dissolved in acetonitrile (32 mL) To the solution was added drop-wise at room temperature (over a 2 minute period) a solution of 2-[(2-hydroxybenzoyl)oxy]benzoic acid (2.20 g, 8.52 mmol) in acetonitrile (20 mL). A white solid precipitated immediately upon addition. After stirring for 1 h at room temperature, the mixture was chilled to 0° C. for 1 h. The white solid was filtered and the solid was washed with 20 mL ice-cold acetonitrile. The material was dried for 5 minutes on the fit followed by transfer of the solid to a round-bottom flask and the material was left under high vac overnight to yield 3.17 g (96%) of 2 as a white solid. MP 152-154° C.; $^1$H NMR (400 MHz, MeOD) 8.12 (dd, J=8.09, 1.66 Hz, 1 H), 7.81 (dd, J=7.67, 1.66 Hz, 1 H), 7.51 (m, 1 H), 7.44 (m, 1 H), 7.30 (m, 1 H), 7.19 (d, J=8.09 Hz, 1 H), 6.96 (m, 2 H), 3.02 (s, 6 H); $^{13}$C NMR (101 MHz, MeOD) 173.63, 169.87, 163.43, 161.27, 160.61, 149.81, 136.91, 134.12, 132.46, 131.46, 131.33, 127.01, 123.96, 120.02, 118.99, 114.90, 38.09.

EXAMPLE 3

The solubility of the compounds of Examples 1 and 2 in water was compared with that of salicylic acid and salicylsalicylic acid.

Measurement of the water solubility of the test compounds is accomplished by using methods well known to those skilled in the art. Specifically, to a weighed amount of the test compounds of Examples 1 and 2 Distilled water is added in small portions until a clear solution is obtained. The total volume of the solution is measured. The water solubility is calculated by dividing the weight of the salt, in mg, by the volume of solution, mL. The water solubility of the compounds of Example 1 and Example 2, respectively, when measured using the above technique, was determined to be 900 mg/mL, and 36 mg/mL.

I claim:

1. A compound selected from the group consisting of compounds of the formula:

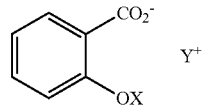

Formula VI and compounds of the formula

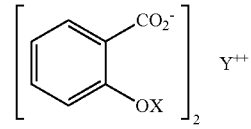

Formula VII wherein X is selected from $R^1$, $R^2$, and $R^3$, wherein $R^1$ is

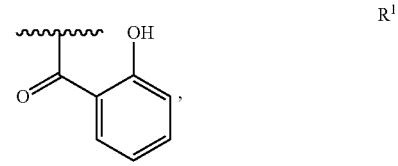 [SMILES: *C(=O)c1ccccc1O]

and R² is

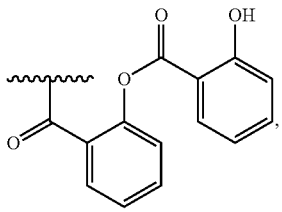

and R³ is

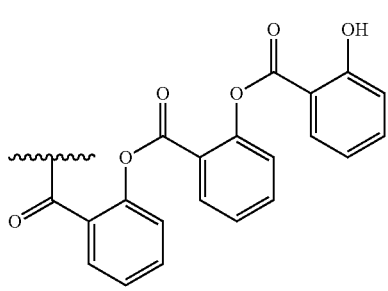

and Y⁺ is H₃N⁺—C(=NH)—NH—C(=NH)—N—(CH₃)₂ and Y⁺⁺ is H₃N⁺—C(=NH)—NH—C(=N⁺H)—N—(CH₃)₂.

2. A compound of the Formula VI in claim 1 wherein X and Y⁺ are as defined in claim 1.

3. A compound of the Formula VII in claim 1 wherein X and Y⁺⁺ are as defined in claim 1.

4. A compound according to claim 2 wherein X is

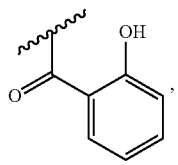

and Y+is H3N+—C(=NH)—NH—C(=NH)—N—(CH3)2, also known by the United States Adopted Name, {[Amino(imino)methyl]amino}(dimethylamino)methaniminium 2-[(2-hydroxybenzoyl) oxy] benzoate.

5. A pharmaceutical composition comprising a compound according to claim 1 and a pharmaceutically acceptable carrier.

6. A pharmaceutical composition comprising a compound according to claim 2 and a pharmaceutically acceptable carrier.

7. A pharmaceutical composition comprising a compound according to claim 3 and a pharmaceutically acceptable carrier.

8. A pharmaceutical composition comprising a compound according to claim 2 wherein X is R¹ and Y⁺⁺ is as defined in claim 2.

9. A pharmaceutical composition comprising a compound according to claim 3 wherein X is R¹ and Y⁺⁺ is defined in claim 3.

10. A kit comprising: a) a unit dosage comprising the compound of claim 1; b) instructions on how to use the kit; and c) at least one container for holding the unit dosage forms.

11. A kit comprising: a) a unit dosage comprising the compound of claim 2; b) instructions on how to use the kit; and c) at least one container for holding the unit dosage forms.

12. A kit comprising: a) a unit dosage comprising the compound of claim 3; b) instructions on how to use the kit; and c) at least one container for holding the unit dosage forms.

13. A kit comprising: a) a unit dosage comprising the compound of claim 5; b) instructions on how to use the kit; and c) at least one container for holding the unit dosage forms.

14. A method of treating diabetes in a mammal, including a human, comprising administering to a mammal, including a human, in need of said treatment a compound according to claim 1.

15. A method of treating diabetes in a mammal, including a human, comprising administering to a mammal, including a human, in need of said treatment an antidiabetic effective amount of a compound according to claim 1.

16. A method of treating diabetes in a mammal, including a human, comprising administering to a mammal, including a human, in need of said treatment an antidiabetic effective amount of a compound according to claim 2.

17. A method of treating diabetes in a mammal, including a human, comprising administering to a mammal, including a human, in need of said treatment an antidiabetic effective amount of a compound according to claim 3.

18. A method of treating diabetes in a mammal, including a human, comprising administering to a mammal, including a human, in need of said treatment an antidiabetic effective amount of a compound according to claim 5.

19. A method of treating pre-diabetes in a mammal, including a human, comprising administering to a mammal, including a human, in need of said treatment a pre-antidiabetic effective amount of a compound according to claim 1.

20. A method of treating pre-diabetes in a mammal, including a human, comprising administering to a mammal, including a human, in need of said treatment an antidiabetic effective amount of a compound according to claim 2.

21. A method of treating pre-diabetes in a mammal, including a human, comprising administering to a mammal, including a human, in need of said treatment a pre-antidiabetic effective amount of a compound according to claim 3.

22. A method of treating pre-diabetes in a mammal, including a human, comprising administering to a mammal, including a human, in need of said treatment a pre-antidiabetic effective amount of a compound according to claim 5.

23. A method for the manufacture of the composition of claim 1 comprising: a) freshly preparing the free base of metformin from a suitable metformin salt; and b) reacting in solvent the freshly prepared free base of metformin with salicylic acid, salicylsalicylic acid, trisalicylic acid or tetrasalicylic acid at a temperature between about 0 degrees C. and about 60 degrees C.

24. A method for the manufacture of the composition of claim 1 comprising: a) freshly preparing the free base of metformin from a suitable metformin salt; and b) reacting the freshly prepared free base of metformin with salicylic acid, salicylsalicylic acid, trisalicylic acid or tetrasalicylic acid at a temperature between about 100 degrees C. and about 200 degrees C.

25. A kit comprising: a) a unit dosage comprising the compound of claim 1; b) instructions on how to use the kit; and c) at least one container for holding the unit dosage forms.

26. A kit comprising: a) a unit dosage comprising the compound of claim 2; b) instructions on how to use the kit; and c) at least one container for holding the unit dosage forms.

* * * * *